United States Patent [19]

Morita et al.

[11] 4,313,929

[45] Feb. 2, 1982

[54] METHOD OF MEASUREMENT OF ANTIGENS AND ANTIBODIES

[75] Inventors: Shiro Morita, Tokyo; Masanobu Sawai, Yamato; Shin-ichro Matsumoto, Tokyo; Tadamitsu Sudo, Sagamihara, all of Japan

[73] Assignee: Mitsubishi Chemical Industries Limited, Tokyo, Japan

[21] Appl. No.: 3,797

[22] Filed: Jan. 16, 1979

[30] Foreign Application Priority Data

Feb. 16, 1978 [JP] Japan ................................. 53/16757

[51] Int. Cl.³ ............................................. G01N 33/54
[52] U.S. Cl. ..................................... 424/12; 23/230 B;
356/339; 356/340; 422/56; 424/8; 424/13; 424/78
[58] Field of Search .................... 424/8, 11, 12, 13, 78; 23/230; 422/55, 56, 105; 356/338, 339, 340

[56] References Cited

U.S. PATENT DOCUMENTS

| | | | |
|---|---|---|---|
| 3,984,533 | 10/1976 | Uzgiris | 424/12 |
| 4,011,044 | 3/1977 | Uzgiris | 23/230 B |
| 4,118,192 | 10/1978 | Sawai | 424/12 |
| 4,174,952 | 11/1979 | Cannell | 424/12 |
| 4,203,724 | 5/1980 | Sawai | 23/230 B |
| 4,205,954 | 6/1980 | Babson | 23/230 B |
| 4,208,185 | 6/1980 | Sawai | 23/230 B |
| 4,224,304 | 9/1980 | Sawai | 424/12 |

FOREIGN PATENT DOCUMENTS 1384399 2/1975 United Kingdom .................. 424/12

OTHER PUBLICATIONS

Dezelic, Croatica Chem. Acta, vol. 42, 1970, pp. 457–466.
Dezelic, Eur. J. Biochem., vol. 20, 1971, pp. 553–560.
Cohen, Immunochem., vol. 12, 1975, pp. 349–351.
Williams (Ed.) Methods in Immunology & Immunochem., Acd. Press, N.Y., vol. II 1968, pp. 163–181.

*Primary Examiner*—Anna P. Fagelson
*Attorney, Agent, or Firm*—Oblon, Fisher, Spivak, McClelland & Maier

[57] ABSTRACT

A method of the quantitative measurement of antigens and antibodies by reacting an antigen or antibody or a mixture thereof with the corresponding antibody and/or antigen which has been supported on insoluble carrier particles, irradiating the resulting reaction mixture with light of a specific wavelength to measure the intensity of light scattered by the reaction mixture.

21 Claims, 6 Drawing Figures

METHOD OF MEASUREMENT OF ANTIGENS AND ANTIBODIES

BACKGROUND OF THE INVENTION

1. Field of the Invention

This invention relates to a method of the measurement of antigens and antibodies. More particularly, this invention relates to a method of the quantitative measurement of antigens and antibodies by supporting an antibody or an antigen on insoluble carrier particles having minute particle diameters to sensitize the insoluble carrier particles, then reacting the sensitized carrier with a corresponding antigen, antibody or mixture thereof and irradiating the reaction mixture with light of a specific wavelength to measure the intensity of light scattered by the reaction mixture.

2. Description of the Prior Art

There is a continuing need for rapid, accurate, qualitative and quantitative determinations of biologically active substances, e.g., antigens, antibodies, at extremely low concentrations. Today, there is a wide need for determining the presence of drugs in body fluids. In addition, in medical diagnosis, it is frequently important to know the presence of various substances which are synthesized naturally by the body or ingested.

Heretofore it has been known to detect antibodies or antigens semiquantitatively by reacting latex particles on which an antibody or an antigen is supported with a corresponding antigen or antibody on a glass plate and observing visually the agglutination state.

In recent years, it was proposed in the following articles to quantitatively determine antigens and antibodies using the above-mentioned latex particles by supporting the corresponding antibody or antigen on the latex particles to sensitize the latex, reacting the supported antibody or antigen with the antigen or antibody to be determined to agglutinate the latex particles, and measuring the rate of decrease in turbidity of the supernatant of the latex by means of visible lights for the determination of the antigen or antibody utilizing the agglutination phenomena of the latex reagent:

(A) CROATICA CHEMICA ACTA, 42, (1970), p.p. 457–466; and (B) European Journal of Biochemistry, Vol. 20, No. 4, (1971), p.p. 558–560.

Since the method of the above proposal utilizes the measurement of rate of decrease in turbidity to determine the antigen or antibody, it is necessary to use an antibody- or antigen-sensitized latex of an extremely low concentration, for example, in the range of 0.007 to 0.028%, to carry out the reaction of the latex and the antigen or antibody in a stationary state, to remove any impurity of affecting the turbidity from the sample to be tested, and the like.

As a result, the above-mentioned method is disadvantageous in that the rate of the antigen-antibody reaction is inevitably decreased, both the precision and the reproducibility are insufficient for the determination technique of antigens or antibodies, and that the removal of impurities sometimes requires extremely complicated operations. Accordingly it is difficult to apply the above method to the determination of such antigen as fibrinogen (Fg), human chlorionic gonadotropin (hCG) or the like, since it requires complicated procedures for the preparation of its reagent and it is difficult to cause reproducible agglutination reaction if it is present in blood or urine which also contains various other substances capable of adversely affecting the reaction.

Also in the article, (C) Immunochemistry, Vol. 12, p.p. 349–351 (1975) it was proposed to determine quantitatively antibodies and antigens by irradiating the above-mentioned agglutinated latex particles with a laser beam and measuring the change in width of spectral lines of the scattered light of the laser beam in order to determine the mean diffusion constant ($\overline{D}$) which gives an indication of the Brownian motion of the agglutinated particles which in turns is inversely proportional to the size of the agglutinated particles.

Also in this method, since the antibody- or antigen-sensitized latex is used in an extremely low concentration, for example, as low as 0.001%, the rate of the antigen-antibody reaction is so decreased that both the precision and the reproducibility become poor. In addition, this method is also disadvantageous in that it requires complicated calculation using the technique of spectrum analysis which in turn requires complicated operations, and that any impurity in the sample must be removed prior to the measurement. Accordingly, this method has not been put into practice as well.

The above paper C also described that determination by the turbidity method as reported in the foregoing paper A gives extremely imprecise results (FIG. 2 on page 350 of the same). Accordingly, the object of this invention is to provide a method for the rapid determination of an antigen and/or antibody in a sample to be tested with a high precision and a good reproducibility.

SUMMARY OF THE INVENTION

This object can be accomplished by reacting an antigen or antibody or a mixture thereof with the corresponding antibody and/or antigen which has been supported on insoluble carrier particles having an average diameter of not greater than 1.6 microns, said reaction being carried out in a liquid medium, irradiating the resulting reaction mixture with light of a wavelength in the range of 0.8 to 2.4 microns at one or more points of time after the reaction has been started, and measuring the intensity of the light scattered by the reaction mixture.

DETAILED DESCRIPTION OF THE PREFERRED EMBODIMENTS

Figure 1:
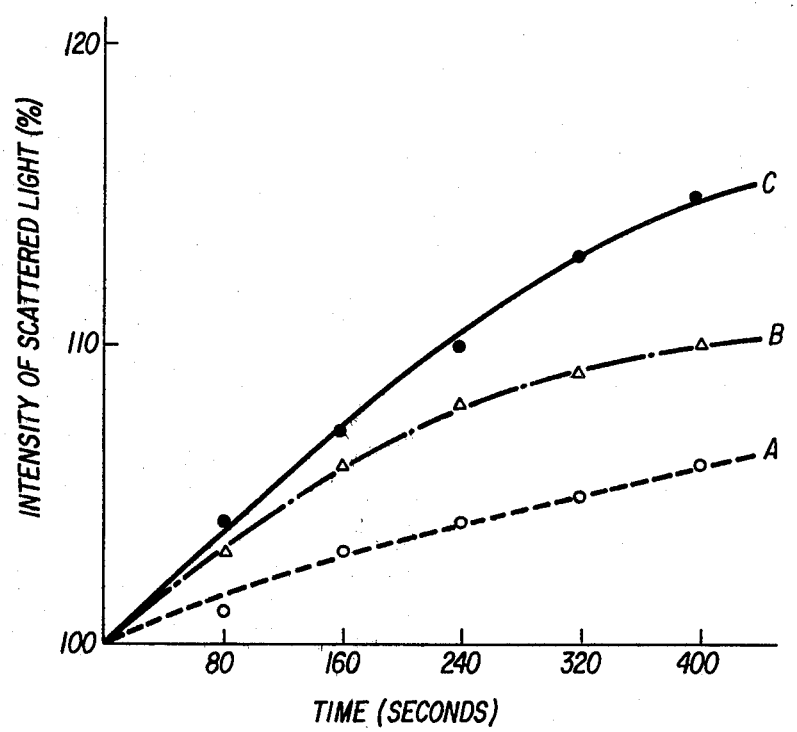
FIG. 1 is a graph which shows the change of intensity of scattered light with time when the reaction mixture of a standard Fg solution of a concentration of 2.0 μg/ml and a mixture of polystyrene latices having average diameters of 0.091 and 0.220 micron sensitized with anti-(Fg) antibody is irradiated with light of a wavelength of 1.0 micron (A), 1.1 micron (B) or 1.25 micron (C)

In accordance with the method and apparatus of this invention, an extremely small amount of an antigen and/or antibody which could heretofore be determined practically only by the radioimmunoassay (RIA) method can be determined with a precision equal to or higher than that of the RIA method and much more rapidly and safely.

Also, in accordance with the method and apparatus of this invention, it is possible to determine not only multivalent antigens, but incomplete, antigens such as, for example, haptens with high precisions, and the antigens and/or antibodies can be determined not only through their agglutination reaction, but through their agglutination inhibition.

Other objects and advantages of this invention will become apparent from the following more detailed description of this invention.

The light used in this invention has an wavelength in the range of 0.8 to 2.4 microns which falls under the near infrared region or a part of the visible region closely adjacent thereto. Among the light of the above-mentioned region, particularly preferred is the light of the near infrared region having a wavelength in the range of 1.0 to 1.8 microns.

It has now been found that, if an antigen and/or antibody in a sample is reacted with the corresponding antibody and/or antigen supported on microparticles of an insoluble carrier having an average diameter of not greater than 1.6 microns, preferably in the range of 0.1 to 1 micron and more preferably from 0.2 to 0.8 micron in order to cause agglutination of the microparticles and the resulting reaction mixture is irradiated with light of the above-mentioned near infrared region having a wavelength longer than the average diameter of the carrier particles, preferably by a factor of at least 1.5 and more preferably at least 2, the intensity of the light scattered by the reaction mixture increases in good proportion to the progress of the agglutination caused by the antigen-antibody reaction. Thus it is important for the practice of this invention to select the wavelength of the applied light and the average diameter of the carrier properly so that a certain correlation is established between the concentration of a particular antigen or antibody or a mixture thereof (including the reaction product) in a sample solution and the intensity of light scattered by the reaction mixture.

When a beam of light falls upon a semitransparent body, part of the light is scattered, part is absorbed and part is transmitted. If the intensity of the incident beam is equal to $I_o$, that of the scattered light to $I_s$, that of the absorbed light to $I_a$ and that of the transmitted light to $I_t$, the following relation holds;

$$I_o = I_s + I_a + I_t \tag{1}$$

In the system which this invention concerns, since the absorption of the light can be substantially neglected, Equation (1) can be rewritten as:

$$I_o = I_s + I_t \tag{2}$$

When the incident beam falls on microparticles suspended in a transparent liquid as in the case of this invention, the light is scattered in every direction. Among the scattered light, the forwardly scattered light, that is, the scattered light passing in the direction of incidence combines with the true transmitted light and thereby constitutes the apparent transmitted light. The intensity of such apparent transmitted light varies with the progress of the antigen-antibody reaction.

This invention is directed to the measurement of the remaining components of the total scattered light exclusive of the component parallel to the incident beam (the intensity of said parallel component being denoted by $I_s''$), or in other words, the light scattered in directions other than that of the incident beam (the intensity of said light being denoted by $I_s'$). Of course, the following relation holds:

$$I_s = I_s' + I_s'' \tag{3}$$

The insoluble carrier particles useful for this invention include those organic polymer microparticles which are substantially insoluble in the particular liquid medium used for the measurement according to the invention and which have an average diameter within the above-mentioned range, such as, for example, latices of organic polymers such as polystyrene and styrene-butadiene copolymer obtained by emulsion polymerization; dispersed coccal bacteria such as staphylococci and streptococci, *Bacillus prodigiosus*, rickettsia, cell membrane fragments, etc.; as well as microparticles of inorganic oxides such as silica, silica-alumina and alumina, and finely pulverized minerals, metals and the like.

In accordance with the invention, an antibody or an antigen which is reactive with the antigen and/or antibody in the sample to be measured is supported on the above-mentioned insoluble carrier particles such as, for example, latex particles (i.e., to sensitize the carrier). For this purpose, the antibody or antigen may be physically and/or chemically adsorbed on the carrier.

Antibodies consist of proteins, whereas antigens are composed of one member selected from various substances such as, for example, proteins, polypeptides, steroids, polysaccharides, lipids, pollen, dust and the like. There have already been proposed a number of methods for supporting these antibodies or antigens, particularly antibodies on insoluble carrier particles.

When an incomplete antigen, particularly a hapten is supported on insoluble carriers, it is advantageous to chemically modify the carrier, for example, with a coupling agent and subsequently chemically adsorb the antigen on the modified carriers.

In accordance with this invention, the insoluble carrier particles (e.g., latex particles) sensitized with an antibody or antigen (these particles being hereinafter referred to as "sensitized carrier particles") can be used as a suspension containing these particles in a rather high concentration of at least 0.05% by weight, preferably from 0.1% to 1%, more preferably from 0.2% to 0.6% in order to provide such conditions that the antigen or antibody in a sample can react with the sensitized carrier particles as actively as possible. Also, in accordance with this invention, the reaction between the antigen- or antibody-containing sample and the sensitized carrier particles can be effected under non-standing conditions. For this purpose, it is advantageous to carry out the reaction with agitation including stirring and shaking.

The antigen-antibody reaction of this invention is carried out in a liquid medium, preferably in water or a mixture of water and a water-miscible organic solvent such as methanol, ethanol, acetone, etc.

In one embodiment of this invention, an antigen- or antibody-containing sample solution which may be diluted or concentrated is reacted with a suspension of insoluble carrier particles on which the corresponding antibody or antigen has been supported, thereby causing the agglutination of the particles. In another embodiment, a sample solution which contains an antibody or antigen to be determined is reacted first with the corresponding antigen or antibody and the resulting reaction mixture is then reacted with a suspension of insoluble carrier particles on which the corresponding antibody or antigen has been supported.

In the method of this invention, the reaction mixture thus obtained is irradiated with light of a particular wavelength at one or more points of time after the reaction has been started and the intensity of light scattered by the reaction mixture is measured to determine the antigen or antibody in the sample.

In practice, this may be accomplished by any of the following procedures:

(A) From a standard sample containing a known amount of an antigen and/or antibody, a set of dilute standard samples are prepared by diluting the original standard sample by various factors. Each of the diluted and undiluted standard samples is reacted with insoluble carrier particles sensitized with a definite amount of the corresponding antibody or antigen. The reaction is continued for a given period of time (e.g., from a few minutes to 2 hours) under predetermined conditions, for example, at room temperature. At this time, the intensity of light scattered by the reaction mixture is measured. From the data thus obtained, a standard curve (A) which indicates the relationship between the amount (concentration) of the antigen or antibody in the standard solution and the intensity of the scattered light is prepared for the particular combination of the antigen and/or antibody and the sensitized carrier particles. Subsequently, an unknown sample is reacted with the same sensitized carrier particles under substantially the same conditions as used in the preparation of Standard Curve A. After the same reaction time has elapsed, the intensity of the light scattered by the reaction mixture is measured and compared with Standard Curve A, whereby the amount (or concentration) of the antigen and/or antibody in the unknown sample can be determined.

(B) It is possible to prepare another type of Standard Curve B which indicates the relationship between the reaction time (e.g., from several seconds to 10 minutes at room temperature) required for the intensity of the scattered light to reach a certain value and the amount (concentration) of the antigen or antibody in standard sample. An unknown sample is similarly reacted with the same sensitized carrier particles under the same conditions as used in the preparation of this standard curve. The determination of the amount or concentration of the antigen and/or antibody in the unknown sample can be effected by measuring the time required for the intensity of the light scattered by this reaction mixture to reach the same value and comparing it with Standard Curve B.

(C) A standard sample containing a known amount of an antigen and/or antibody is diluted by various factors to prepare a set of dilute standard samples. Each of these diluted and undiluted samples is reacted under predetermined conditions with insoluble carrier particles sensitized with a definite amount of the corresponding antibody or antigen and the intensity of the scattered light is measured at two or more points of time in such a stage that the reaction of the mixture proceeds steadily and the intensity of the light scattered by the reaction mixture increases almost steadily for the first time soon (e.g., at least 2 to 3 seconds, preferably at least 5 seconds) after the start of the reaction. From the data thus obtained, Standard Curve C which indicates the relationship between the amount (concentration) of the antigen or antibody in the sample and the rate of increase in intensity of the scattered light per unit time is prepared for the paritcular combination of the antigen and/or antibody and the sensitized carrier particles. Subsequently, an unknown sample is reacted with the same sensitized carrier particles under substantially the same conditions as used in the preparation of Standard Curve C and the rate of increase in intensity of the scattered light per unit time is determined in substantially the same way. By comparing the value thus obtained with Standard Curve C, it is possible to determine the amount or concentration of the antigen and/or antibody in the unknown sample.

In the method of this invention, the intensity of scattered light may be measured with an integrating sphere used for spectroscopic analyses of usual emulsive samples wherein the area of the inner surface of the integrating sphere which the incident beam falling on the sample cell and transmitted thereby reaches straightly is painted black. Alternatively, the measurement of scattered light may be conveniently carried out with the conventional device for the measurement of light scattering.

Having generally described this invention, a more complete understanding can be obtained by reference to certain examples which are provided herein for purpose of illustration only and are not intended to be limiting in any manner.

EXAMPLE 1

(1) Preparation of anti-fibrinogen-antibody-sensitized latex (anti-Fg-latex) reagent:

To 10 ml of a solution of anti-(human fibrinogen (Fg)) antibody in a glycine buffer containing 2 mg/ml of Fg, 0.5 ml of a polystyrene latex of an average diameter of 0.091 micron (Dow Chemical Co., 10 wt. % solids content) and 0.5 ml of another polystyrene latex of an average diameter of 0.220 micron (ditto) were added. The mixture was stirred for 30 minutes at room temperature, then warmed to 40° C. and further stirred for an additional 30 minutes at that temperature. After the reaction mixture was centrifuged for 50 minutes at 12,000 r.p.m. under cooling at 2°–4° C., the precipitates were collected by decantation and the isolated anti-Fg-antibody-sensitized latex particles were suspended in a 0.2 wt. % solution of bovine serum albumin so as to prepare an anti-Fg-sensitized latex reagent containing 0.5% by weight of the sensitized latex particles.

(2) Reaction of anti-Fg-sensitized latex and Fg antigen:

To 0.2 ml of the anti-Fg-sensitized latex reagent prepared in Part (1) above, 0.2 ml of a standard Fg solution having a concentration of 2 μg/ml and dissolved in an isotonic sodium chloride solution containing 0.1 wt. % bovine serum albumin was added and thoroughly mixed. The resulting mixture was placed in a cell of 2 mm (thickness)×10 mm (width)×40 mm (length) and irradiated with light of a wavelength of 1.0, 1.1 or 1.25 microns. During the irradiation, the change of intensity of the scattered light with time was measured and recorded with Hitachi 340 spectrophotometer to which Hitachi 340-0702 attachment, an integrating sphere, and a PbS detector were attached. In the area of the sphere opposite to the sample cell, a filter paper coated with black ink was placed instead of the referential white board. The reference cell (2 mm thick) contained an equivolume mixture of the sensitized latex reagent and the isotonic sodium chloride solution containing 0.1 wt. % bovine serum albumin (said mixture being hereinafter referred to as "blank"), and in the area opposite to the reference cell, the referential white board was used as it was.

The results are shown in FIG. 1 of the accompanying drawing. The intensity of the scattered light appearing in the ordinate of FIG. 1 denotes the ratio of $I_s/I_o$ in percentage wherein $I_o$ represents the intensity of the scattered light measured with the above-mentioned device when both the sample and reference cells contain the blank mixture, and $I_s$ represents that when the sample cell contains the actual reaction mixture containing Fg antigen.

Figure 2:
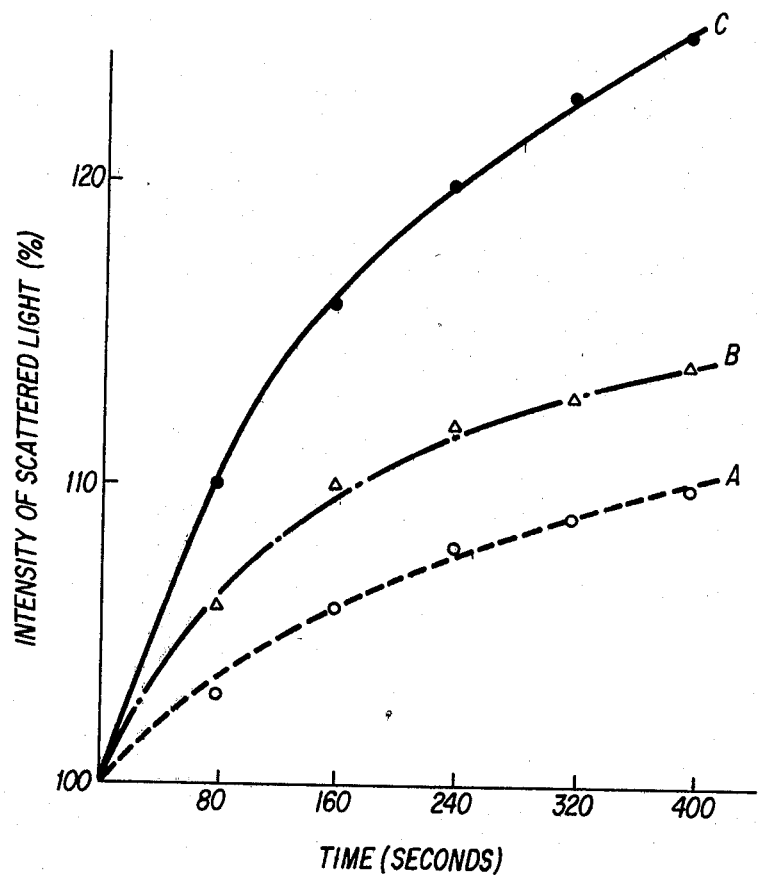
FIG. 2 is a graph similar to FIG. 1 in which the standard Fg solution has a concentration of 0.5 μg/ml.

Using another standard Fg solution having a concentration of 0.5 μg/ml, the above-mentioned procedure was repeated and the results as shown in FIG. 2 were obtained.

In FIG. 1 and FIG. 2, A, B and C indicate the results obtained at wavelengths of 1, 1.1 and 1.25 microns, respectively. It can be seen from FIG. 1 and FIG. 2 that favorable results can be obtained by using an incident beam of a wavelength of at least 1 micron, preferably at least 1.2 microns for the measurement of scattered light, and that the intensity of scattered light varies depending on the concentration of the antigen.

EXAMPLE 2

(1) Preparation of calibration curve:

To 0.2 ml of an anti-Fg-sensitized latex reagent prepared in exactly the same way as described in Example 1, 0.2 ml of each standard Fg solution (in the isotonic sodium chloride solution described in Example 1) having a concentration indicated in Table-A below was added and thoroughly mixed.

Figure 3:
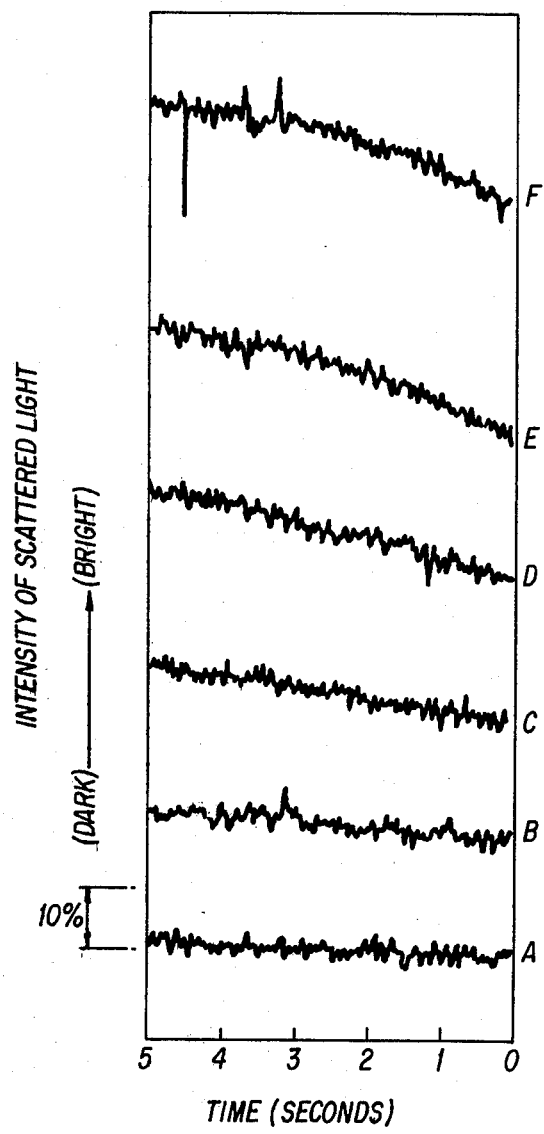
FIG. 3 is a chart which shows the change of intensity of scattered light with time when the reaction mixture of one of standard Fg solution at various concentrations and an anti-Fg-sensitized latex is irradiated with light of a wavelength of 1.25 microns.
Figure 4:
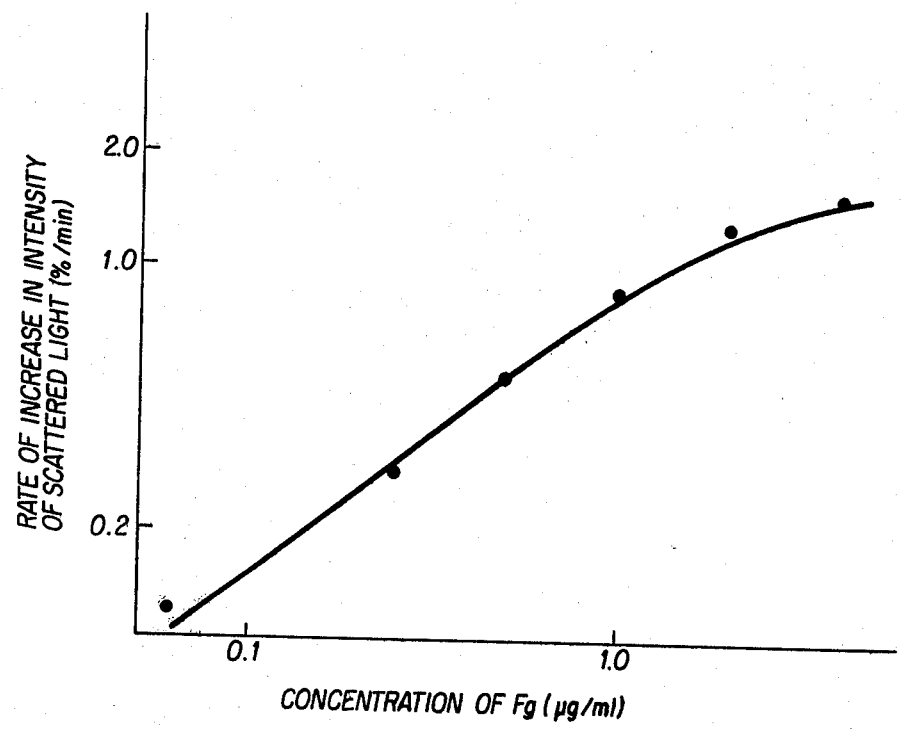
FIG. 4 is a graph which shows the relationship between the rate of increase in intensity of scattered light and the concentration of standard Fg solution obtained from the data of FIG. 3.

Thereafter the measurements of scattered light was taken at a wavelength of 1.25 microns as in Example 1 and the change of intensity of the scattered light with time was continuously recorded. The resulting chart is shown in FIG. 3, in which Curves A, B, C, D, E and F correspond to Fg concentrations of 0.0625, 0.250, 0.500, 1.00, 2.00 and 4.00 μg/ml, respectively, and the unit on the ordinate is identical to that described in Example 1. A straight line was drawn on each curve along its approximately straight portion appearing in the earliest stage after the recording had been started. From the slope of each straight line thus drawn, the rate of change (increase) in intensity of the scattered light per unit time was obtained and plotted as ordinate against the concentration of antigen as abscissa. Thus a calibration curve as shown in FIG. 4 was obtained.

TABLE - A

| Fg concentration (μg/ml) | Rate of increase in intensity of scattered light (%/min.) |
|---|---|
| 0.0625 | 0.12 |
| 0.250 | 0.29 |
| 0.50 | 0.51 |
| 1.00 | 0.87 |
| 2.00 | 1.29 |
| 4.00 | 1.57 |

The amounts of Fg in unknown samples could be determined from the calibration curve as follows:

(2) Assay of Fg in unknown samples:

A sample of blood or urine was collected from a subject and if the sample is blood, the serum was separated therefrom in the conventional manner. If necessary, the sample was then diluted by the factor indicated in Table-B below. Following the procedure as described in Part (1) above, 0.2 ml of the undiluted or dilute sample was mixed with 0.2 ml of the anti-Fg-latex reagent prepared in Part (1) of Example 1 and the resulting reaction mixture was irradiated with light of a wavelength of 1.25 micron in order to determine the rate of increase in intensity of the scattered light. On the calibration curve prepared in Part (1), the value of Fg concentration corresponding to the observed rate of increase in scattered light was read. The results are shown in Table-B.

For the purpose of comparison, Table-B also involves the data obtained in accordance with the conventional radioimmunoassay (RIA) method (S. M. Ratkey, et al., Brit. J. Hematol., 30, 145-149, 1975) and the slide method (Fujimaki, Tamura and Takahashi, Rinsho Kagaku (Clinical Science), 12, 507, 1976, Japan; and Fujimaki, Ikematsu, Takeuchi and Kato, Rinsho Byori (Japanese Journal of Clinical Pathology), 21, 973, 1973).

TABLE B

| Subject No. | Unknown sample Material | Unknown sample Dilution factor | Rate of increase in intensity of scattered light (%/min.) | Fg concentration in unknown sample (μg/ml) Method of this invention | Fg concentration in unknown sample (μg/ml) RIA method | Fg concentration in unknown sample (μg/ml) Slide method |
|---|---|---|---|---|---|---|
| 1 | Urine | × 16 | 0.37 | 4.96 | 5.021 | 8.0 |
| 2 | " | × 1 | 0.34 | 0.27 | 0.337 | 0.5 |
| 3 | Serum | × 10 | 0.185 | 1.20 | 1.230 | 1.25 |

EXAMPLE 3

To 0.2 ml of an anti-Fg-sensitized latex reagent prepared in exactly the same manner as in Example 1, 0.2 ml of each standard Fg solution having a concentration indicated in Table-C below and prepared in the same manner as in Example 1 was added and thoroughly mixed. The resulting mixture was transferred to the sample cell as used in Example 1 and irradiated with light of a wavelength of 1.25 microns. Using a stop watch, the intensity of the scattered light was measured 2 minutes after the reaction mixture was placed in the cell. The intensity ($I_s$) of the scattered light after two minutes is converted to the increment (delta, $\Delta$) of the intensity on the basis of $I_o$, that is, the intensity of scattered light obtained by measuring the blank mixture used in Example 1, said increment Δ being represented by the equation:

$$\Delta = (I_s/I_o - 1) \times 100$$

Figure 5:
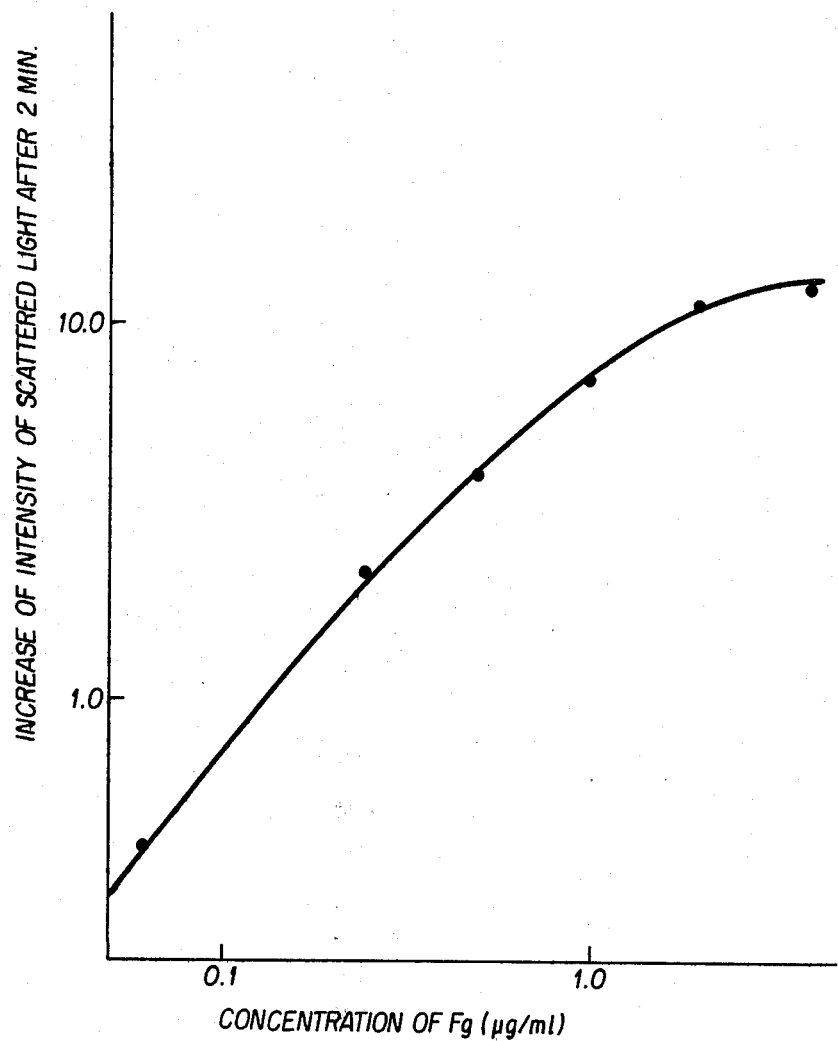
FIG. 5 is a calibration curve which shows the relationship between the increment in intensity of scattered light after 2 minutes from the start of the reaction and the concentration of Fg when the reaction mixture of one of standard Fg solutions at various concentrations and an anti-Fg-sensitized latex is irradiated with light of a wavelength of 1.25 microns.

The results obtained at various concentrations of standard Fg solutions are shown in Table-C. From the data in Table-C, the calibration curve of FIG. 5 which showed the correlation between the concentration of antigen (Fg) and the increment of intensity of the scattered light after a given period of time was obtained. Using this calibration curve, it is possible to determine the concentrations of Fg in unknown samples.

TABLE C

| Fg concentration (μg/ml) | Increment of intensity of scattered light after 2 min. (%) |
|---|---|
| 0.0625 | 0.4 |
| 0.250 | 2.2 |
| 0.50 | 4.0 |
| 1.00 | 7.2 |
| 2.00 | 11.6 |
| 4.00 | 12.6 |

EXAMPLE 4

Figure 6:
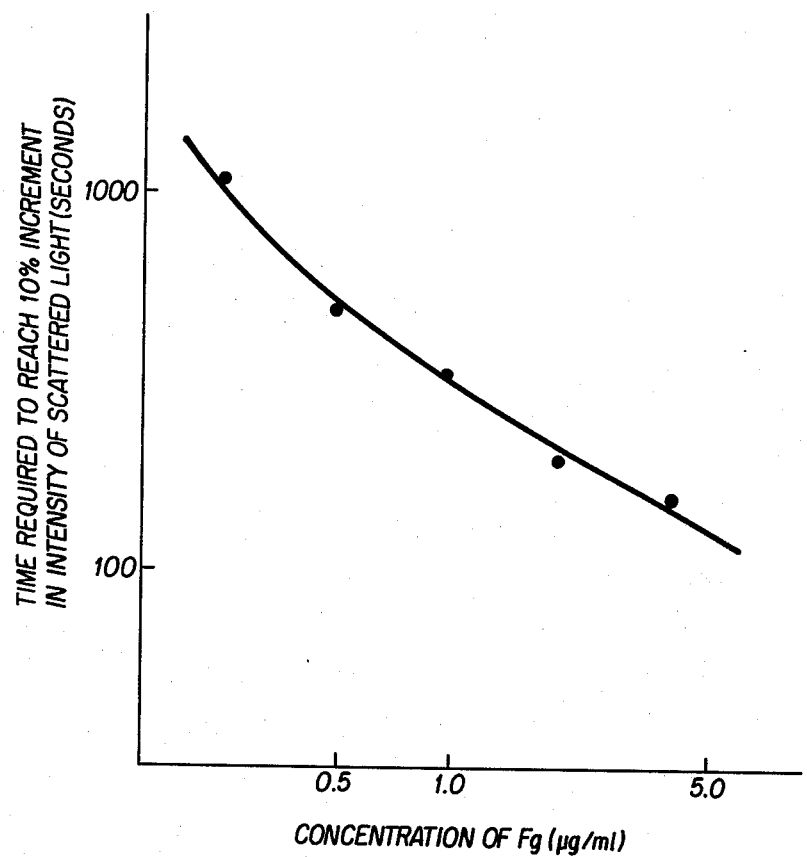
FIG. 6 is a calibration curve which shows the relationship between the time required to reach 10% increment in intensity of scattered light and the concentration of Fg when the reaction mixture of one of standard Fg solutions at various concentrations and an anti-Fg-sensitized latex is irradiated with light of a wavelength of 1.25 microns.

To 0.2 ml of an anti-Fg-sensitized latex reagent prepared in exactly the same manner as Example 1, 0.2 ml of each standard Fg solution having a concentration indicated in Table-D below and prepared in the same way as Example 1 was added and thoroughly mixed. The resulting mixture was transferred to the sample cell used in Example 1 and irradiated with light of a wavelength of 1.25 microns. Immediately thereafter the measurement of intensity of the scattered light was started and the time required for the increment (Δ) of intensity of the scattered light as defined in Example 3 to reach 10% was measured with a stop watch from the starting time of the measurement. The results are shown in Table-D and FIG. 6. Using FIG. 6, it is possible to determine the concentrations of Fg in unknown samples.

TABLE D

| Fg concentration (μg/ml) | Time required to reach 10% increment in intensity of scattered light (min.) |
|---|---|
| 0.250 | 1,020 |
| 0.500 | 500 |
| 1.00 | 340 |
| 2.00 | 200 |
| 4.00 | 160 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method for determining antigens and antibodies which comprises reacting an antigen or antibody or a mixture thereof with a corresponding antibody, antigen or mixtures thereof which has been supported on insoluble carrier particles having an average diameter of not greater than 1.6 microns, said reaction being carried out in a liquid medium, irradiating the resulting reaction mixture with light of a wavelength in the range of 0.8 to 2.4 microns at one or more points of time after the reaction has been started, and measuring the intensity of total light scattered by the reaction mixture in the directions other than that of the incident beam.

2. The method according to claim 1 wherein an antigen or antibody to be determined is reacted with the corresponding antibody or antigen supported on the insoluble carrier particles in the liquid medium under predetermined, substantially fixed conditions, and the rate of increase in intensity of the light scattered by the reaction mixture per unit time is evaluated at about a fixed time after the reaction has been started.

3. The method according to claim 2 wherein an antigen or antibody to be determined is reacted with the corresponding antibody or antigen supported on the insoluble carrier particles in the liquid medium under predetermined, substantially fixed conditions, and thereafter the rate of increase in intensity of the light scattered by the reaction mixture per unit time is evaluated in such stage that the reaction proceeds steadily.

4. The method according to claim 3 wherein said rate of increase is evaluated at an early time after the reaction has come to the steady state.

5. The method according to claim 4 wherein an antigen or antibody in a test fluid is reacted with the corresponding antibody or antigen supported on the insoluble carrier particles under predetermined, substantially fixed conditions and thereafter the rate of increase in intensity of the light scattered by the reaction mixture per unit time is evaluated in such stage that said intensity of the light increases steadily by the lapse of time.

6. The method according to claim 1 wherein an antigen or antibody to be determined is reacted with the corresponding antibody or antigen supported on the insoluble carrier particles in the liquid medium under predetermined conditions for a given period of time to measure the intensity of light scattered by the reaction mixture.

7. The method according to claim 1 wherein an antigen or antibody to be determined is reached with the corresponding antibody or antigen supported on the insoluble carrier particles in the liquid medium under predetermined conditions to measure the time required for the intensity of the light scattered by the reaction mixture to reach a given value.

8. The method according to claim 1 wherein the insoluble carrier particles have an average diameter in the range of 0.1 to 1.0 micron.

9. The method according to claim 1 wherein the insoluble carrier particles have an average diameter in the range of 0.2 to 0.8 micron.

10. The method according to claim 1 wherein the reaction mixture is irradiated with light having a wavelength or wavelengths in the range of 1.0 to 1.8 microns.

11. The method according to claim 1 wherein the light has a wavelength which is longer than the average diameter of the carrier particles and at which the intensity of the light scattered by the reaction mixture increases as the reaction proceeds.

12. The method according to claim 11 wherein the light has a wavelength which is longer than the average diameter of the carrier particles by a factor of at least 1.5.

13. The method according to claim 12 wherein the light has a wavelength which is longer than the average diameter of the carrier particles by a factor of at least 2.

14. The method according to claim 1 wherein the carrier particles are present in the reaction mixture at a concentration of at least 0.05% by weight.

15. The method according to claim 14 wherein the carrier particles are present in the reaction mixture at a concentration of 0.1 to 1% by weight.

16. The method according to claim 1 wherein the carrier particles are present in the reaction mixture at a concentration in the range of 0.2% to 0.6% by weight.

17. The method according to claim 1 wherein the liquid medium is water or a mixture of water and a water-miscible organic solvent.

18. The method according to claim 1 wherein a test fluid which may be diluted or concentrated and which contains an antigen or antibody is reacted with a suspension of the carrier particles on which the corresponding antibody or antigen has been supported.

19. The method according to claim 1 wherein a test fluid containing an antibody or antigen to be determined is first reacted with the corresponding antigen or antibody and the resulting reaction mixture is then reacted with a suspension of the carrier particles on which the corresponding antibody or antigen has been supported.

20. The method according to claim 1 wherein an antibody or antigen is supported on the insoluble carrier particles by physical and/or chemical adsorption thereon.

21. The method according to claim 1 wherein an antibody or antigen is supported on the insoluble carrier particles by chemical bonding through a coupling agent.

* * * * *